United States Patent [19]

Stromgren

[11] 4,367,733
[45] Jan. 11, 1983

[54] ANKLE SUPPORT

[76] Inventor: Lawrence T. Stromgren, 2917 Hillcrest Dr., Hays, Kans. 67601

[21] Appl. No.: 172,073

[22] Filed: Jul. 24, 1980

[51] Int. Cl.³ ............................................. A61F 13/06
[52] U.S. Cl. ................................................... 128/166
[58] Field of Search ............ 128/166, 80 H, DIG. 15, 128/166.5, 165, 169, 157

[56] References Cited

U.S. PATENT DOCUMENTS 3,674,023 7/1972 Mann ................................... 128/166

Primary Examiner—John D. Yasko
Attorney, Agent, or Firm—D. A. N. Chase; Michael Yakimo, Jr.

[57] ABSTRACT

A reusable athletic wrap for providing prophylaxis support to the ankle region comprises a socklike elastic sheath with an elongated elastic panel attached thereto. On slipping the sheath over the foot of the wearer, the elongated panel is wrapped about the foot in a predetermined manner to present first and second heel locks to the foot at laterally opposite sides of the ankle. Three sets of Velcro fasteners having paired mating elements therein are positioned along the wrap for mutual interengagement during wrapping. The respective sets of fasteners prevent slippage of the first and second heel locks from their functional position and secures the end portion of the panel about the ankle region at the conclusion of the predetermined manner of wrapping. Furthermore, the use of paired mating elements define associated panel segments which can be selectively stretched in order to offer a selective degree of compression to portions of the foot covered by the panel during the predetermined wrapping path.

9 Claims, 9 Drawing Figures

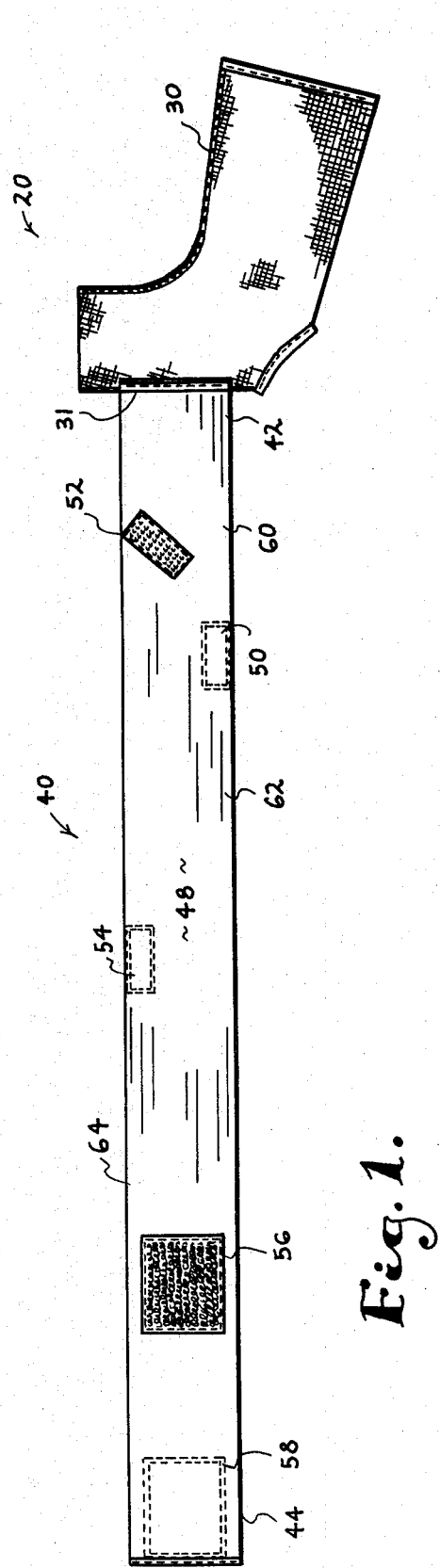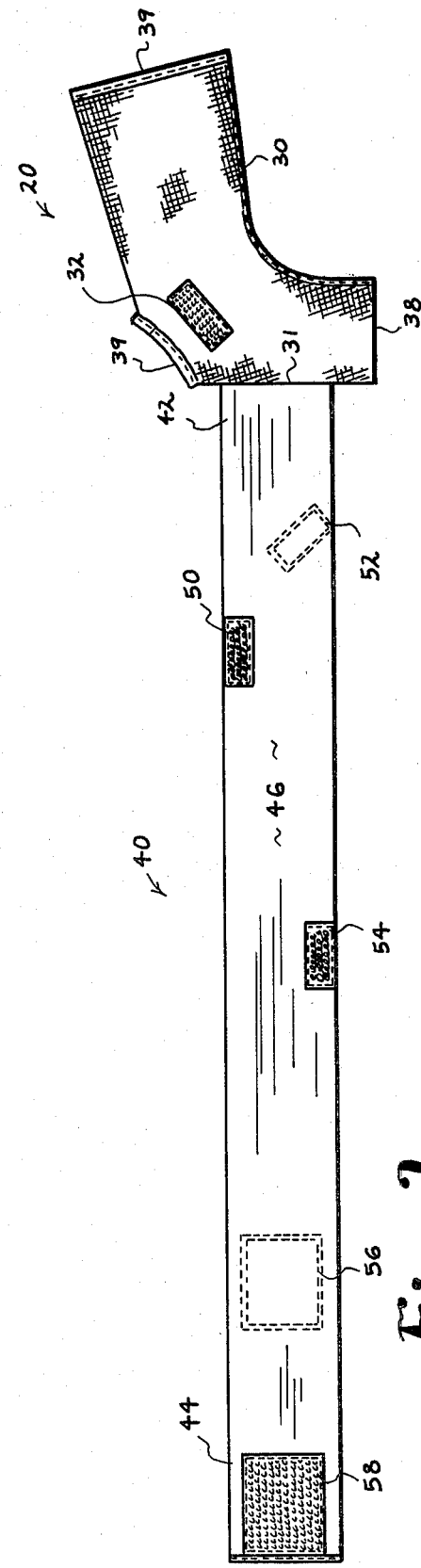

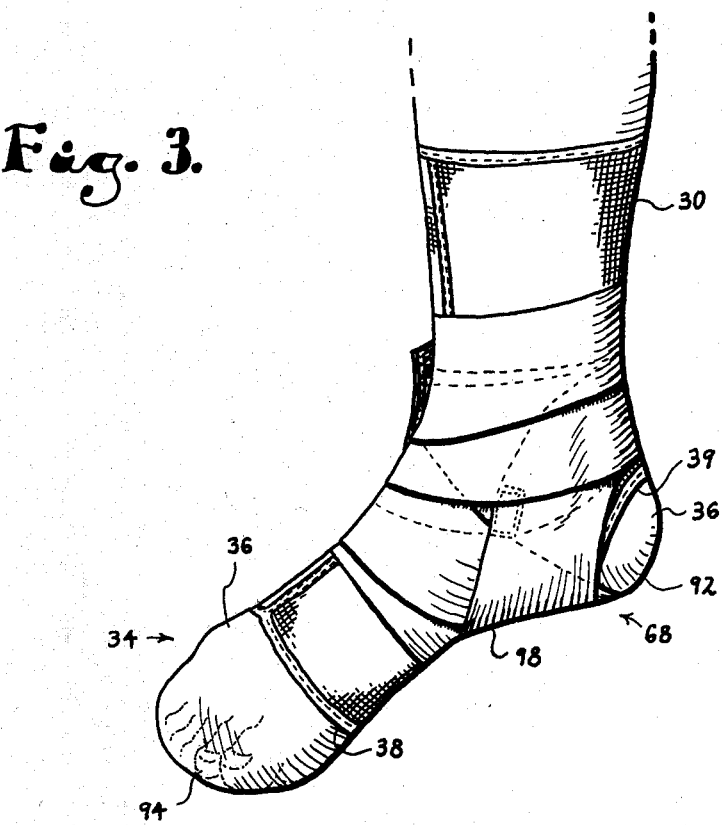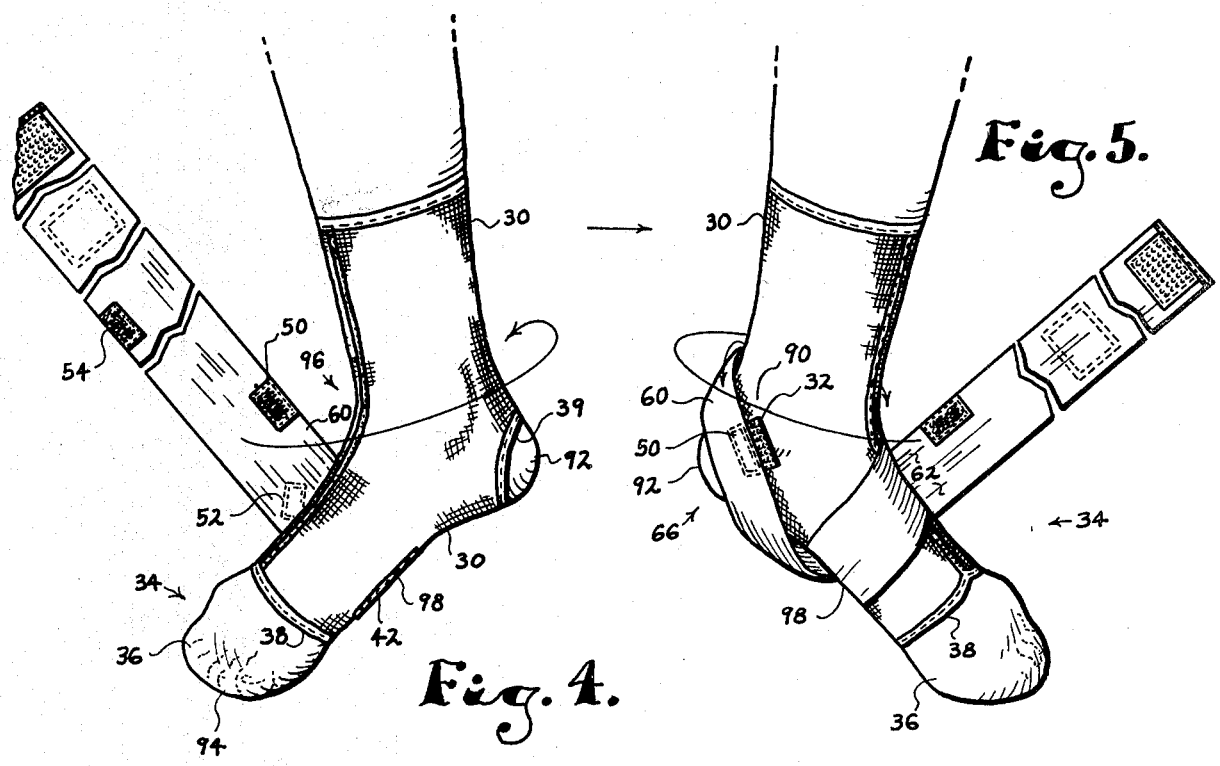

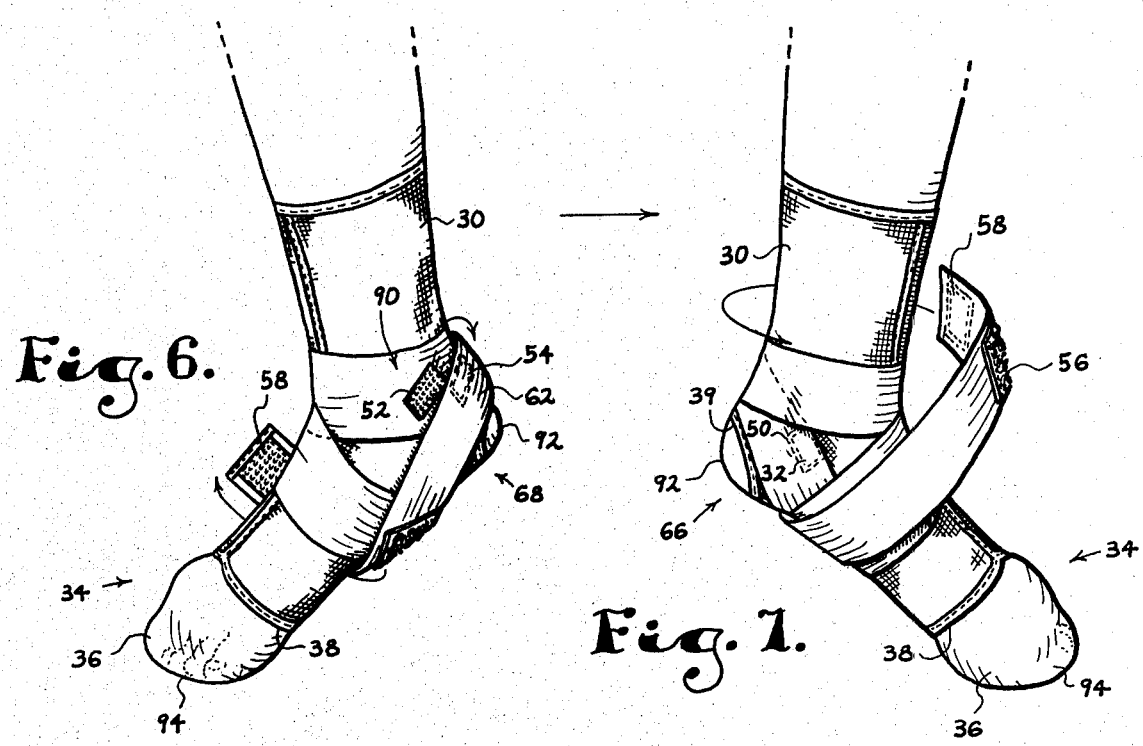
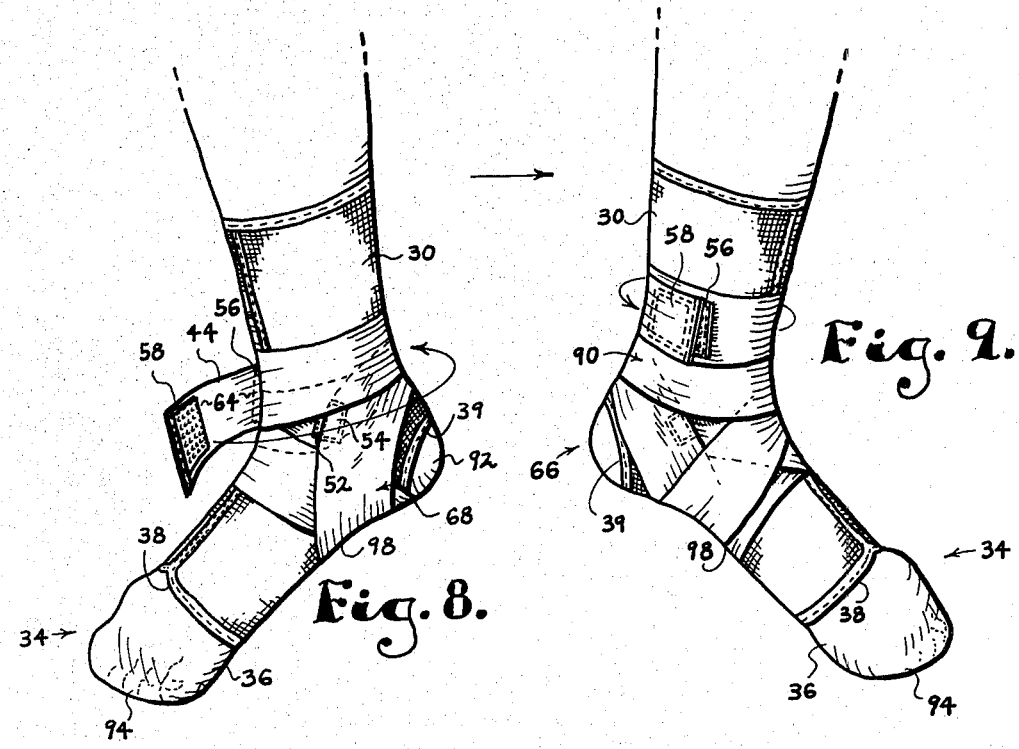

ANKLE SUPPORT

BACKGROUND OF THE INVENTION

This invention relates to a prophylaxis ankle wrap, and more particularly, to an improved ankle wrap having means incorporated therein for maintaining the wrap at predetermined heel lock positions relative to the foot of the wearer as well as providing for selectable adjustment of the compression of portions of the wrap bearing against the foot of the wearer.

It is well accepted that proper taping of the ankle can be of value to prevent debilitating ankle sprains. In response numerous methods of wrapping incorporated into various configurations of ankle supports have been utilized. Either an adhesive tape strapping or a reusable ankle wrap made of various materials have been used to support the ankle in prevention against injury.

In taping of the ankle, whether using an adhesive tape or a canvas-type ankle wrap, the ankle should be wrapped to prevent the foot from turning inward. Furthermore, it is generally accepted that a heel lock should be incorporated in the taping so as to give the ankle added support. A proper ankle wrapping incorporating a heel lock should hinder inversion, eversion and rotation of the ankle. The purpose of the heel lock is to support the ankle and add stability to the heel, which further supports the lateral ligaments of the ankle surrounding that area. A sprain or strain usually occurs when the foot is in planar flexion during forward propulsion which leads to the heel being raised off the ground. Therefore, the ligaments of the ankle area, especially the anterior talofibular and the calcaneo-fibular ligaments should be supported so as to assure tone and stability as prevention against ankle sprains. These ligaments are usually pulled or stretched or partially torn in a normal ankle injury.

This prevention calls for the wrap to be applied in a manner to insure solid, semi-unyielding contact between the bones of the heel, outside ankle knob and the talus. If the heel is so secured, the possibility of ligament strain is reduced. Arch taping can be used to prevent downward lateral strain upon the metatarus (arch bones) and small bones in the ankle joint.

As appreciated, the use of adhesive tape to achieve the above effects can be costly, not only in actual purchase costs, but also in manpower costs as proper taping normally must be applied and/or supervised by the athletic trainer. Accordingly, many configurations of useable ankle wraps have appeared for utilization by both the casual and serious athlete so as to prevent ankle sprains.

Problems have arisen with reusable ankle wraps, including the failure to recognize that the heel locks incorporated therein must be maintained in their proper position, less the wrap slip over the heel during ambulatory action and negate the advantages offered by a heel lock. Also, past ankle wraps have not addressed the ability to allow the wearer to selectively adjust the compression of portions of the ankle wrap offered to the foot of the wearer along the length of the wrap. Previously known ankle wraps had no means of variously adjusting this compression along the longitudinal extent thereof, as no means were incorporated therein to present integral variously compressible segments of the wrap to the wearer. Also, known ankle wraps had no means of guiding the user through the predetermined, desired method of wrapping in order to preclude the possibility of a non-optimal manner of engagement of the ankle wrap about the foot of the wearer.

Accordingly, the instant invention utilizes a predetermined method of wrapping which offers locking of the heel as provided by first and second heel locks (also called a "double heel lock") appearing on opposite lateral sides of the ankle region as well as effective uplift to the arch of the wearer. Disposition of sets of mating fasteners along the ankle wrap provides for maintenance of these heel locks in their respective positions during ambulatory action. Furthermore, this disposition allows the compressive effect of portions of the ankle wrap associated with the mating fasteners to be variously adjusted and maintained thereat as desired by the wearer. The wrap is used in conjunction with an electric socklike sheath which offers a basal compression to the entire ankle region as well as precludes the necessity to anchor the wrap to the skin of the wearer and minimizes blisters appearing on the foot of the wearer. Finally, the use of a plurality of sets of mating fasteners with paired elements therein assures that the desired manner of wrapping is followed as deviation therefrom will not present the mating elements in a proper position for the required mutual engagement therebetween.

It is therefore a general object of this invention to provide an improved reusable ankle wrap which offers prophylaxis support to the ankle of the wearer.

Another general object of this invention is to provide an ankle wrap, as aforesaid, having a predetermined method of wrapping so as to lock the heel of the wearer and which has means thereon designed to maintain the ankle wrap at this heel locking position.

Another general object of this invention is to provide an ankle wrap, as aforesaid, which has means thereon for providing user adjustment of the compression of segments of the wrap in their bearing against the foot of the wearer.

A further object of this invention is to provide an ankle wrap, as aforesaid, which provides effective support to an ankle without restriction of ambulatory action of the wearer.

Still another object of this invention is to provide an ankle wrap, as aforesaid, which is easily fitted to the foot of the wearer without the necessity to anchor the wrap to the skin portion thereof.

A further object of this invention is to provide for an ankle wrap, as aforesaid, having a socklike sheath for fitting over the foot of the wearer and offering a basal compression thereto.

A more particular object of this invention is to provide an ankle wrap, as aforesaid, which provides both a heel lock and arch lift to the foot of the wearer.

Still another object of this invention is to provide an ankle wrap, as aforesaid, which presents a girdle fit to the foot of the user and is not bulky or cumbersome during use.

A still more particular object of this invention is to provide an ankle wrap for use with an athletic sock or the like in order to minimize blisters appearing on the foot of the wearer.

A more particular object of this invention is to provide an ankle wrap, as aforesaid, which has means thereon indicative to the user that the predetermined manner of wrapping is being followed.

Another object of this invention is to provide an ankle wrap, as aforesaid, which is economical to manufacture and is durable and long-lived.

Other objects and advantages of this invention will become apparent from the following description taken in connection with the accompanying drawings, wherein are set forth by way of illustration and example a preferred embodiment of this invention.

BRIEF DESCRIPTION OF THE DRAWINGS

FIG. 1 is a plan view of an ankle wrap for the right foot as taken from the rear side thereof;

FIG. 2 is a plan view of the ankle wrap shown in FIG. 1 taken from the front side thereof;

FIG. 3 is a perspective view, taken from the inside of the right foot, showing the ankle wrap in a position fully secured to the foot of the wearer;

FIGS. 4 through 9 show, in order, the steps of the predetermined method of wrapping and are as follows:

FIG. 4 is a perspective view, taken from the inside of the right foot, showing the socklike sheath slipped over the foot with the elastic panel, being foreshortened for purposes of illustration, at the starting position;

FIG. 5 is a perspective view, taken from the outside of the right foot, showing the presentation of a first heel lock by the elastic panel with the mating engagement of the elements of the first heel lock maintenance means;

FIG. 6 is a perspective view, taken from the inside of the right foot, showing the presentation of a second heel lock by the elastic panel laterally opposite from the first heel lock, as shown in FIG. 5, and prior to the mating engagement of the elements of the second heel lock maintenance means;

FIG. 7 is a perspective view taken from the outside of the right foot, showing the end portion of the elastic panel prior to initiation of a path encompassing the top of the ankle region;

FIG. 8 is a perspective view, taken from the inside of the right foot, showing the encompassment of the end portion of the elastic panel about the ankle region of the wearer;

FIG. 9 is a perspective view, taken from the outside of the right foot showing the final mating engagement of the associated fasteners at the conclusion of the predetermined method of wrapping.

DESCRIPTION OF THE PREFERRED EMBODIMENT

Referring more particularly to the drawings, the ankle wrap 20 generally comprises a socklike sheath 30 made of an elastic material such as Spandex or the like with an elongated panel 40 fastened to the sheath 30 along one panel end 42. The panel 40 is also made of an elastic material and has a plurality of paired Velcro fasteners disposed on the front 46 and rear surfaces 48 therealong.

Located on the sheath 30 is a Velcro fastener 32 positioned laterally adjacent the ankle when the sheath 30 is fitted to the foot 34 of the wearer. The panel 40 is attached to the sheath 30 by sewing the first end 42 thereto at a location preferably adjacent the arch portion 31 of the sheath 30 as shown in FIG. 4. A Velcro mating fastener 50 is longitudinally displaced from the first end 42 and appears on the front surface 46 of the panel 40 in order to releasably engage fastener 32 during the predetermined method of wrapping as to be subsequently explained.

Located on the rear surface 48, between the panel first end 42 and the mating fastener 50 is Velcro fastener 52. The fastener 52 is longitudinally disposed along the panel 40 so as to be presented adjacent the ankle 90 of the wearer and generally laterally opposite the Velcro fastener 32 during wrapping. Displaced from the fastener 52 and beyond the fastener 50 is a mating fastener 54 positioned on the front surface 46 of the panel 40 for releasable engagement to the fastener 52.

Longitudinally displaced from the fastener 52 and positioned adjacent the second end 44 of the panel 40 is a pair of mating Velcro fasteners 56 and 58. These longitudinally spaced apart fasteners 56 and 58 are mounted on opposite surfaces 46 and 48 of the panel 40 for mutual engagement one 56 to the other 58 at the conclusion of the predetermined method of wrapping.

The disposition of the paired fasteners having spaced apart mutually engageable elements therein 32 and 50, 52 and 54, 56 and 58 define associated segments 60, 62 and 64 along the elastic panel 40. These panel segments of the panel 40 are used to provide the first 66 and second 68 heel locks to the foot 34. Segment 64 is wrapped about the top of the ankle region and also assists in the prevention of medial and lateral ankle sprains. Furthermore, the correspondence between the paired fasteners an associated segments allows for each segment 60, 62 and 64 to be selectively compressed about the foot 34 of the wearer during the predetermined method of wrapping.

OPERATION

In operation, the socklike sheath 30 is slipped over the foot 34 of the wearer (the right foot being used for purposes of illustration), the foot preferably having an athletic sock 36 thereon. Upon fitting, the heel 92 and toe 94 regions of the foot 34 protrude through the sheath openings 38, 39 as shown in FIG. 4. The sheath 30 in its operative position compresses the whole region of the foot 34 contained therein, as well as presents a means to mount the first end 42 of the elastic panel 40 to the foot 34 without the necessity to secure the panel 40 directly thereto. Accordingly, the use of the sheath 30 provides a point of connection to the foot 34 and thus prevents irritation to the foot 34 that may result from a direct mounting of the elastic panel 40 thereto. Velcro fastener 32 is concurrently positioned adjacent the ankle 90 at the outside surface 96 thereof.

To initiate wrapping, as shown in FIG. 4, the panel 40 is brought to the outside of the foot 34 and, as indicated by the arrow in FIG. 4, is brought about the front of the ankle 90 region (across the tibia) and to the rear thereof. As shown in FIG. 5, the panel is then downwardly drawn towards the arch 98 along the lateral side of the heel 92 so to prevent the first heel lock 66 thereto. During this initial wrapping, Velcro fastener 50 is presented in an overlying relationship to fastener 32 so as to be mutually engageable therebetween, such engagement maintaining the heel lock 66 in its operative position as shown in FIG. 5. Furthermore, due to the correspondence of the first segment 60 of the panel 40 to the fasteners 32 and 50, this segment 60 can be selectively stretched by the wearer in order to adjust the degree of compression offered by the segment 60 against the foot 34 during the initial wrapping. The range of selectable compression will vary from a basic reference compression which is determined by a full mating engagement of the fasteners 32 and 50 as shown in FIG. 5. Thus, a greater or lesser compression, relative to the basic reference compression can be selected according to the degree of overlap of the fastener 50 with mating fastener 32. This enables the first segment 60 to be drawn about the foot 34 during the initial step of wrapping, with an accompanying selectable degree of compression incorporated into the first heel lock 66 offered thereto.

During this initial wrapping, fastener 52 has been presented on the inside of the foot generally adjacent the ankle 90 region and opposite the fastener 32 as shown in FIG. 6. Subsequently, panel 40 is downwardly drawn towards and under the arch 98 and to the inside of the foot 34 as shown in FIG. 5 so as to uplift the arch 98. The panel 40 is then drawn across the front of the foot 34, around the rear thereof. This step in wrapping is similar, but in an opposite direction, to the initial step as above described. As shown in FIG. 6, the panel 40 is downwardly drawn towards the arch 98 along the lateral inside surface of the heel 92 to present a second heel lock 68. During this wrapping, Velcro fastener 52 is presented in an adjacent relationship to fastener 52 for mating but releasable interengagement so as to maintain this second heel lock 68 in the desired operative position. The associated second segment 62 of the panel 30, including the fasteners 52 and 54, can be selectively stretched so as to adjust the compressive effect of the segment 62 offered to the foot, such compression capable of being varied from the degree of compression offered by the first segment 60. As above described for the first heel lock maintenance means, the degree of compression offered by segment 62 during the provision of the second heel lock 68 to fiit 34 can vary from a basic reference compression as defined by a full mating of the fasteners 52 and 54. Thus, the degree of compression offered to the foot 34, and including the heel 92, by the associated panel segment 62 can vary from this reference compression as well as from that offered by segment 60 during wrapping.

Upon releasable engagement of the fasteners 52 and 54, the third segment 64 of the panel 40 is drawn underneath the arch 98 to offer uplift thereto, towards the opposite side of the foot 34 and about the front of the foot 34 as shown in FIG. 7. A pair of Velcro mating fasteners 56 and 58 located adjacent the panel second end 44 are releasably engaged one to the other upon wrapping of the second end portion 44 about the top of the ankle region, as shown in FIG. 8, which concludes the predetermined method of wrapping. Again, the degree of compressive effect offered by the third segment 64 of the panel 40 to the foot 34 of the wearer corresponds to the degree of engagement of the fasteners 56 and 58. Variance from a full mating engagement of the fasteners 56 and 58 corresponds to a variance of the compressive effect offered by segment 64 to the foot 34 and can vary from that offered by the preceding segments 60, 62 during the foot wrapping path.

Upon conclusion of the wrapping, as shown in FIG. 3 and FIG. 9, the user is provided with inside 66 and outside 68 heel locks, referred to as a "double" heel lock on the lateral sides of the ankle region so as to prevent inversion and eversion of the ankle 90 joint. Also, the wrapping of the arch 98 gives effective uplifting support thereto. This predetermined method of wrapping in conjunction with the compressive effect of the elastic sheath 30 is a highly effective prophylaxis to the ankle 90 region. The continuity of this prophylaxis function, especially as to the maintenance of the effectiveness of the "double" heel lock is assured by the heel lock fasteners, 32 and 50, 52 and 54, located along the panel 40. Thus, the wrap 20 affords an effective support to the ankle 90 region with a cost effective reduction in the time and expense associated with adhesive tape wrapping.

Furthermore, as above discussed, the use of the paired fasteners along the panel 40 and the elastic sheath 30 allows for a selective and variable degree of compression to be offered to the foot of the wearer by associated segments 60, 62 and 64 of the panel 40 as determined by the user during such wrapping. Also, of note is that the paired fasteners offers a visible indication to the user of whether the panel 40 is being wrapped in the proper predetermined manner, as a derivation from the desired manner of wrapping will result in non-alignment of the elements of the fasteners precluding the releasable engagement therebetween.

Although the wrap 20 is described for use with the right foot, it is understood that the wrap is also adaptable for use with the left foot with a reversal of the position of the elements therein and a change in direction of the predetermined method of wrapping. Accordingly, it is understood that this wrap 20 can be used for either foot with identical accompanying advantages and results.

Having then described the invention, what is claimed as new and desired to be secured by Letters Patent is:

1. An ankle wrap comprising:
   a socklike sheath adapted to slip over the foot of the wearer;
   an elongated panel having first and second end portions and made of an elastic material for a compressive wrapping about the ankle and arch of said foot in a predetermined manner to provide lift to said arch and first and second heel locks to said foot on the respective lateral sides of said ankle;
   means for connecting said first end portion of said panel to said sheath;
   heel lock maintenance means on said wrap for holding in an operative position at least one of said heel locks presented by said elongated panel and including fastener elements on said panel disposed about said foot during said wrapping for mutual interengagement; and
   means along said second end portion for securing said portion to said foot upon conclusion of said wrapping whereby to maintain said at least one heel lock on said foot of the wearer.

2. The apparatus as claimed in claim 1, further comprising:
   a second heel lock maintenance means on said wrap holding in position the other of said heel locks presented by said predetermined method of wrapping and including fastener elements on said wrap disposed about said foot during said wrapping for mutual interengagement whereby to maintain a double heel lock on said foot of the wearer.

3. The apparatus as claimed in claim 1, wherein said one of said heel locks is said first heel lock and said associated maintenance means comprises:
   a first fastener element mounted on said sheath adjacent said ankle of the wearer; and
   a second fastener element on said panel and longitudinally displaced from said first end portion, said second fastener element presented adjacent said first fastener element during provision of said first heel lock by said predetermined manner of panel wrapping for mutual interengagement, whereby said first and second engaged elements prevents slippage of said panel from said first heel lock position.

4. The apparatus as claimed in claim 1, wherein said one of said heel locks is said second heel lock and said associated maintenance means comprises:
a first fastener element mounted on said panel and longitudinally displaced from said first end portion; and
a second fastener element mounted on said panel and longitudinally displaced from said first fastener element towards said second end portion, said first fastener element presented adjacent the ankle of said foot during said predetermined method of wrapping with said second fastener element presented adjacent said first fastener element during provision of said second heel lock by said predetermined method of panel wrapping for mutual interengagement whereby said first and second engaged elements prevent slippage of said panel from said second heel lock position.

5. An ankle wrap comprising:
a socklike sheath adapted to slip over the foot of the wearer;
an elongated panel having first and second end portions and made of an elastic material for wrapping about the ankle and arch of said foot in a predetermined manner to provide lift to said arch and first and second laterally spaced-apart heel locks to said foot;
means on said wrap for selecting the degree of compression of segments of said panel offered to said foot during said predetermined wrapping and comprising:
at least two sets of fastener means disposed along said sheath and said panel with each set of fastener means having longitudinally spaced-apart first and second mating elements defining associated sgements of said panel therebetween and utilized in said respective first and second heel locks, said first and second fastener elements of each set releasably engageable during said predetermined manner of wrapping; and
means associated with each pair of mating elements for varying the degree of engagement therebetween from a full mating engagement, said degree of mating element engagement variously tensioning said associated segment and corresponding to a degree of compression offered by said associated panel segment to said foot during said wrapping.

6. The apparatus as claimed in claim 5, wherein said respective variable engagement means comprises:
first and second mating fasteners providing for said pair of mating elements with each fastener having an elongated configuration extending along the direction of said wrapping for mutual interengagement between variable portions thereof to provide for said degree of mating element engagement, said degree of fastener engagement corresponding to a stretching of said associated panel segment whereby to present said compression offered to said foot.

7. An ankle wrap comprising:
a sock-like sheath adapted to slip over the foot of the wearer;
an elongated panel having first and second longitudinally spaced-apart end portions and made of an elastic material for wrapping about the ankle and arch of said foot in a predetermined manner to provide first and second heel locks to said foot on the respective lateral sides of said ankle;
means for connecting said first end portion of said panel to said sheath;
a first heel lock fastener means including first and second fastener elements positioned respectively on said sheath and said panel and defining a panel segment therebetween utilized in said first heel lock provision, said first and second fastener elements disposed on one lateral side of said ankle in a mutually engaging relationship to pilot said wearer through said predetermined manner of wrapping and said first heel lock provision and to preclude slippage of said associated panel segment and said first heel lock from an operative position;
a second heel lock fastener means including third and fourth fastener elements positioned on said panel and defining a panel segment therebetween utilized in said second heel lock provision, said third and fourth fastener elements disposed on the opposed lateral side of said ankle in a mutually engaging relationship to pilot said wearer through said predetermined method of wrapping and said second heel lock provision and to preclude slippage of said associated panel segment and said second heel lock from an operative position; and
a third fastener means along said second end portion for securing the remaining portion of said panel about said foot upon conclusion of said wrapping whereby said plurality of fastener means maintains said wrap and said heel locks on said foot of the wearer.

8. The apparatus as claimed in claim 7 wherein said first and second fastener elements are selectably engageable in a manner to selectably tension said defined panel segment and effect the compression of said first heel lock on the foot of the wearer.

9. The apparatus as claimed in claims 7 or 8 wherein said third and fourth fastener elements are selectively engageable in a manner to selectably tension said defined panel segment and effect the compression of said second heel lock on the foot of the wearer.

* * * * *